(12) United States Patent
Lam et al.

(10) Patent No.: US 10,668,264 B2
(45) Date of Patent: **\*Jun. 2, 2020**

(54) DELIVERY ADAPTER

(71) Applicant: MicroVention, Inc., Aliso Viejo, CA (US)

(72) Inventors: Jonathan Lam, Anaheim Hills, CA (US); Scott Pool, Laguna Hills, CA (US)

(73) Assignee: MicroVention, Inc., Aliso Viejo, CA (US)

( \* ) Notice: Subject to any disclaimer, the term of this patent is extended or adjusted under 35 U.S.C. 154(b) by 50 days.

This patent is subject to a terminal disclaimer.

(21) Appl. No.: 15/803,694

(22) Filed: Nov. 3, 2017

(65) Prior Publication Data

US 2018/0064922 A1    Mar. 8, 2018

Related U.S. Application Data

(63) Continuation of application No. 14/578,164, filed on Dec. 19, 2014, now Pat. No. 9,833,604.

(60) Provisional application No. 61/919,664, filed on Dec. 20, 2013.

(51) Int. Cl.
| | |
|---|---|
| *A61M 25/16* | (2006.01) |
| *A61M 25/18* | (2006.01) |
| *A61M 39/00* | (2006.01) |
| *A61M 39/10* | (2006.01) |
| *A61M 31/00* | (2006.01) |

(52) U.S. Cl.
CPC ...... *A61M 39/10* (2013.01); *A61M 2039/0009* (2013.01); *A61M 2039/1077* (2013.01); *Y10T 29/49716* (2015.01)

(58) Field of Classification Search
CPC .. A61M 2039/0009; A61M 2039/1077; A61M 39/10; A61M 2005/3206; A61M 5/343; A61M 5/34; A61M 5/3293; A61M 2039/1027; A61M 2039/1083; A61M 2039/1088; A61M 2039/1094; A61M 39/105

See application file for complete search history.

(56) References Cited

U.S. PATENT DOCUMENTS

| | | |
|---|---|---|
| 4,187,848 A | 2/1980 | Taylor |
| 5,122,123 A | 6/1992 | Vaillancourt |
| 5,509,911 A | 4/1996 | Cottone, Sr. et al. |
| 6,511,472 B1 | 1/2003 | Hayman et al. |
| 7,195,615 B2 | 3/2007 | Tan |

FOREIGN PATENT DOCUMENTS

| | | |
|---|---|---|
| EP | 1243285 B1 | 4/2005 |
| WO | WO 2009/045793 A1 | 4/2009 |

OTHER PUBLICATIONS

WIPO, U.S. International Search Authority, International Search Report and Written Opinion dated Apr. 20, 2015 in International Patent Application No. PCT/US2014/071711, 9 pages.

*Primary Examiner* — Rebecca E Eisenberg
(74) *Attorney, Agent, or Firm* — Inskeep IP Group, Inc.

(57) ABSTRACT

A delivery adapter which may be used as an interface between a syringe and a catheter hub is described.

26 Claims, 7 Drawing Sheets

DELIVERY ADAPTER

RELATED APPLICATIONS

This application is a continuation of U.S. patent application Ser. No. 14/578,164 filed Dec. 19, 2014 entitled Delivery Adapter, which claims priority to U.S. Provisional Application Ser. No. 61/919,664 filed Dec. 20, 2013 entitled Liquid Embolic Delivery Adapter, both of which are hereby incorporated herein by reference in their entireties.

BACKGROUND OF THE INVENTION

A delivery adapter may be used as an interface between a syringe and a catheter hub. The syringe may contain a liquid material, in particular a high viscosity liquid material such as liquid embolic. Liquid embolic can be thought of as biocompatible glue which can be used to fill various vascular malformations such as aneurysm, arteriovenous malformation, fistula, or other malformations. Liquid embolic can also be used for various occlusive purposes such as vessel shutdown, fallopian tube occlusion, or occlusion of the peripheral vasculature. The delivery adapter helps to minimize or even eliminate altogether the dilution of the viscous liquid material in the catheter used to deliver said viscous liquid material to a treatment site within the vasculature.

SUMMARY OF THE INVENTION

A delivery adapter is described.

In one embodiment a delivery adapter includes a proximal connector, distal connector, micro-tube, and bridging piece.

In another embodiment a delivery adapter includes a proximal connector, distal connector, micro-tube, bridging piece, and distal rotating element.

In another embodiment methods of delivering a viscous liquid material using the delivery adapter embodiments are described.

DESCRIPTION OF EMBODIMENTS

For the description below the terms proximal and distal are used in regards to particular Figures. Please note generally the term proximal refers to items at the top part of the Figures and the term distal refers to items at the bottom part. The delivery adapter described is connected to a syringe at the top or proximal end, and to a catheter hub at the bottom or distal end. The delivery adapter, when oriented for delivery, may not necessarily sit in a vertical, top-down manner as shown in most of the figures (i.e. adapter may sit laterally, left-to-right or right-to-left depending on the delivery configuration).

Liquid embolic is generally delivered from a syringe to a catheter and then from the catheter to a location within the vasculature of a patient. The embolic material flows through the syringe, into the catheter hub, where the hub 22 includes a tapered reservoir 24 which leads into a smaller diameter channel 26 and the rest of the catheter (see FIG. 1).

Due to the tapered shape of the reservoir 24, it is possible for saline or DMSO or other fluids to remain in the reservoir after those liquids have been used to flush the catheter reservoir 24 and hub 22. When liquid embolic is subsequently delivered, the remaining flushing liquid (e.g., saline or DMSO) may mix with the liquid embolic, thereby diluting the liquid embolic. An adapter provides an interface to deliver the liquid embolic from the syringe to the catheter while minimizing contact with the catheter hub reservoir and thereby minimize or even eliminate any dilution of the liquid embolic by the flushing liquid.

Figure 1:
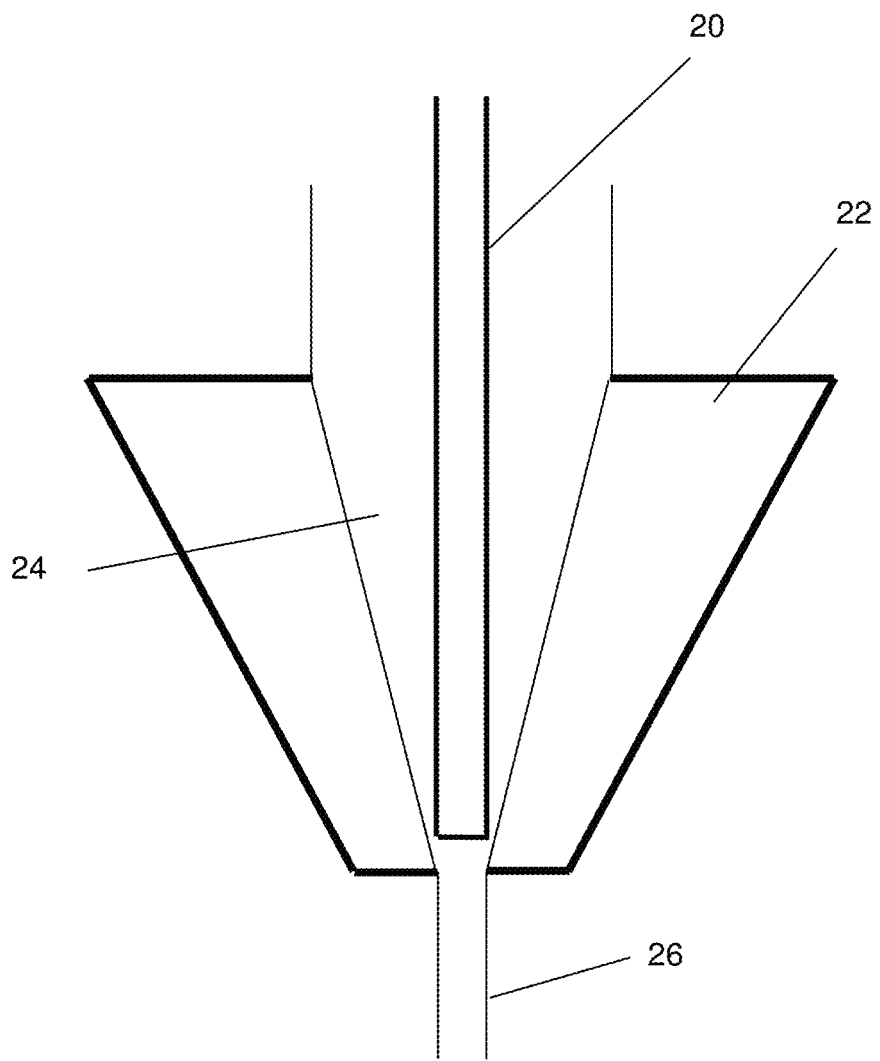
FIGS. 1-2 are schematic views of a catheter hub in accordance with the present invention.

The adapter includes a micro-tube 20 through which the liquid embolic is delivered and which sits within the catheter hub. In FIG. 1 the micro-tube 20 sits in the distal part of the catheter reservoir 24, thus minimizing potential mixing with any flushing fluid retained in the reservoir 24.

Figure 2:
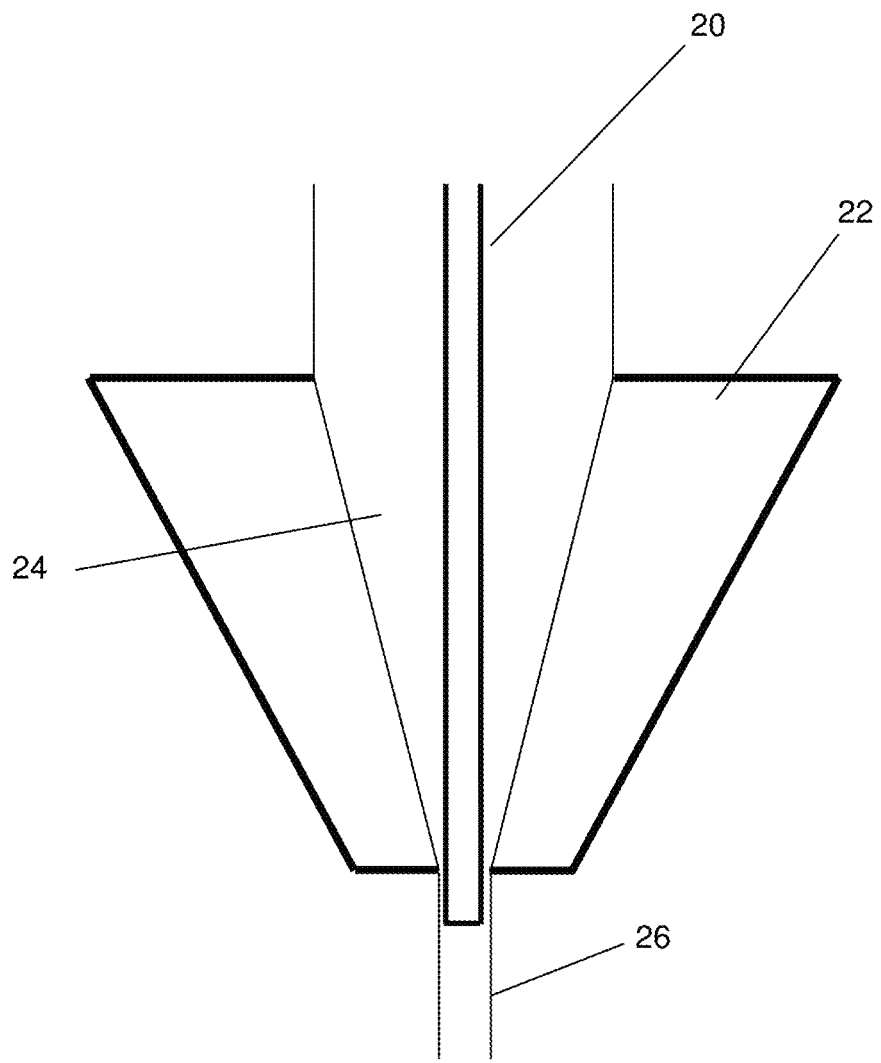

In FIG. 2, the micro-tube 20 bypasses the reservoir entirely and sits within the smaller diameter channel 26. The adapter described may adopt either configuration within the catheter hub 22 shown in FIGS. 1-2, based on the size of the reservoir 24 and length of the micro-tube 20.

Figure 3:
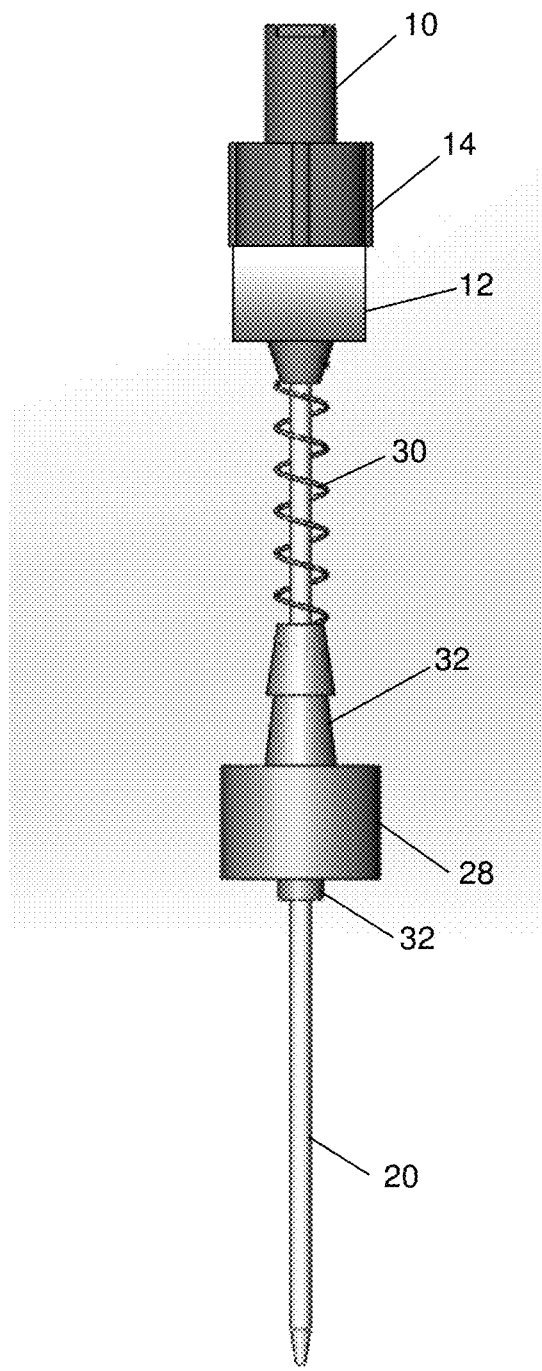
FIG. 3 is a plan view of a delivery adapter according to one embodiment of the present invention.

FIG. 3 shows an embodiment of a delivery adapter comprising a proximal connector 12, distal connector 28, micro-tube 20, and bridging piece 30 which sits between the proximal and distal connectors 12, 28. The proximal connector 12 may be made of a polymer and may include a mating section 10 in the form of a male luer which connects with the female connector of a syringe. The proximal connector 12 may also include a roughed section 14 to aid the user in gripping the adapter to screw and unscrew said adapter from the syringe. In one example the micro-tube 20 is recessed and captured within a portion of the proximal connector 12. In one example the proximal connector 12 contains a channel in which the micro-tube sits. The micro-tube 20 runs from the proximal connector 12 past distal connector 28. Bridging piece 30 sits between proximal connector 12 and distal connector 28.

In the embodiment shown in FIG. 3, the bridging piece 30 is shown as a spring which can be made of a metallic material. In one example, distal connector 28 may be made of a polymer. Distal connector 28 may include a channel 32 which runs through said connector 28. Micro-tube 20 runs through channel 32. In one example, the bridging piece 30 is glued within proximal connector 12 and sits within channels in distal connector 28. This configuration would enable rotation of the bridging piece 30 (e.g., a spring) when the distal connector 28 is not connected to the catheter hub and the user torques proximal connector 12. In one example, the distal end of micro-tube 20 extends about 5-40 mm past distal connector 28. In another example, the distal end of micro-tube 20 extends about 10-20 mm past distal connector 28. In another example, the distal end of micro-tube 20 extends about 15 mm past distal connector 28. The syringe, when mated to proximal connector 12 via mating section 10, connects directly to micro-tube 20 which sits within the proximal connector 12. Thus the syringe contents are directly transferred into the micro-tube of the adapter, and out the distal end of the micro-tube 20 into the catheter hub when the catheter hub is connected to distal connector 28.

Figure 4:
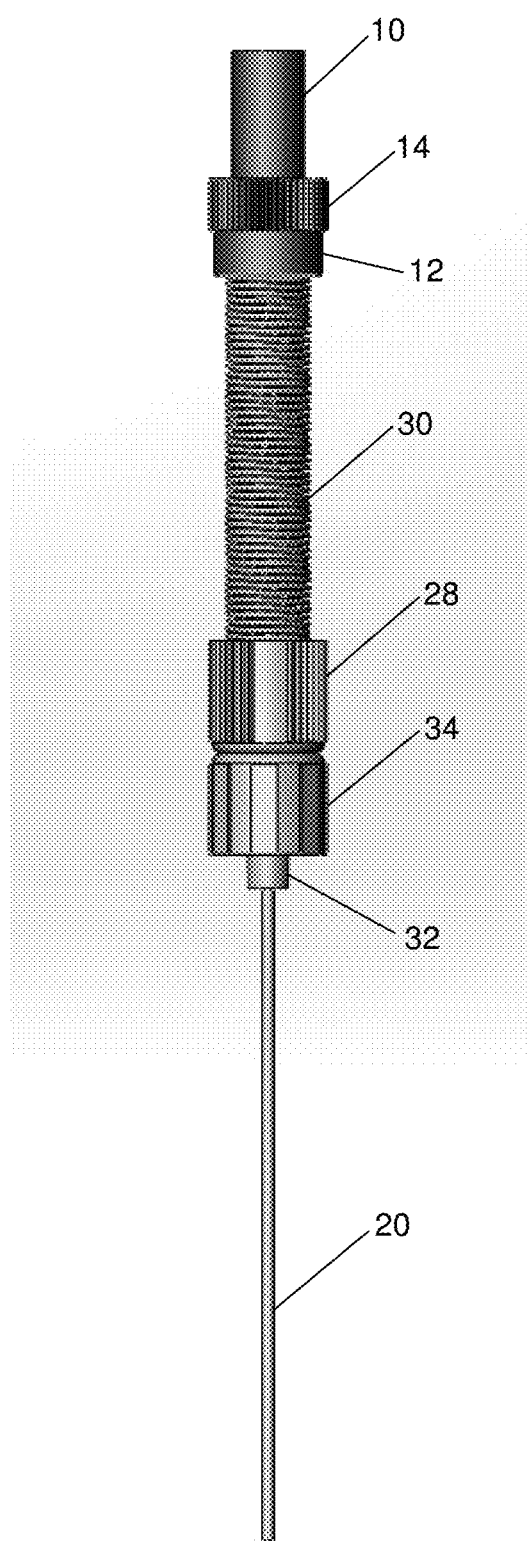
FIG. 4 is a plan view of a delivery adapter according to another embodiment of the present invention.
Figure 5:
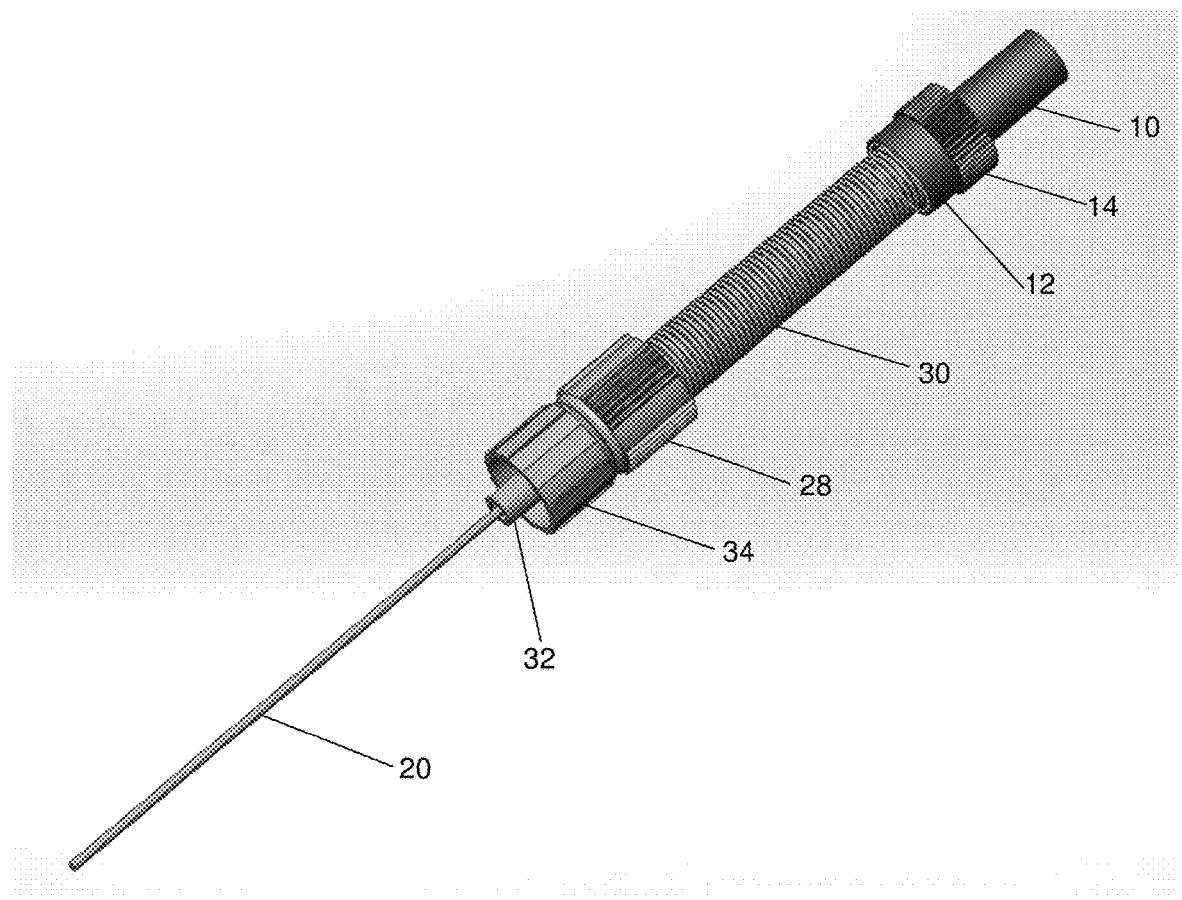
FIG. 5 is a perspective view of the delivery adapter of FIG. 4.

FIGS. 4-5 show another embodiment of a delivery adapter showing an additional distal rotating element 34 which sits just distal of distal connector 28. In one example, bridging piece 30 is glued into proximal connector 12 (e.g., via UV glue) and glued into distal connector 28. Any torquing of the proximal connector 12 by the user prior to attaching the adapter to the catheter hub will result in twisting of distal connector 28. In one embodiment, distal rotating element 34 is free to rotate independent of and/or relative to distal connector 28. The rotational capability of element 34 eases some of the stress on spring bridging element 30 that can otherwise be caused by unilateral torsional stress which may build up on one part of the spring/bridging element, particularly after the adapter is secured to the catheter hub.

Micro-tube 20 may be comprised of a polymer in one example, or a metallic material in another example.

Another embodiment could utilize a threaded bridging piece 30 instead of the spring bridging piece 30 shown in FIG. 3. The threaded bridging piece 30 could be formed of a metallic or polymeric material and would have threads on the surface.

Figure 6:
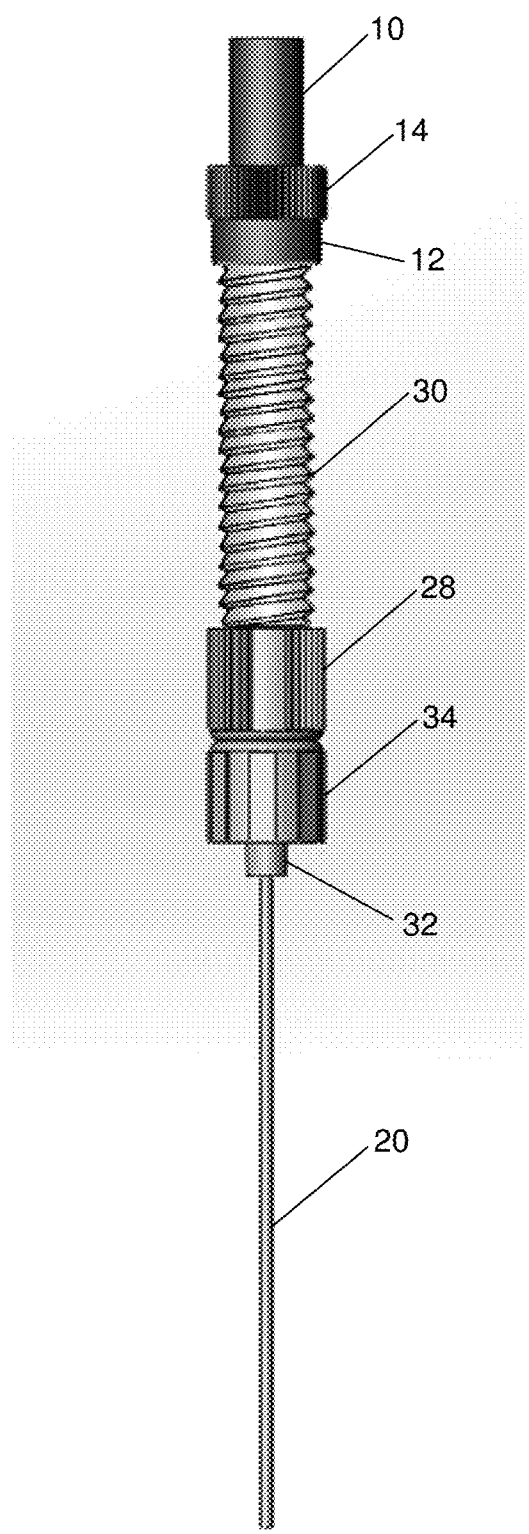
FIG. 6 is a plan view of a delivery adapter according a further embodiment of the present invention.

In one example the bridging piece 30 has external projecting threads and distal connector 28 has corresponding recesses to mate with said threads as shown in FIG. 6, thus rotation of the distal connector 28 will cause upwards or downwards (proximal or distal) movement of distal connector 28. In another example the bridging piece 30 has internal recesses and distal connector 28 has corresponding threads to mate with said recesses, thus rotation of the distal connector 28 will cause upwards or downwards (proximal or distal) movement of distal connector 28. For the embodiment shown in FIGS. 4-5, either distal connector 28 or distal rotating element 34 may have the threads or recesses to mate with the bridging element 30. Alternatively, for the embodiment shown in FIGS. 4-5, both distal connector 28 and distal rotating element 34 may have the threads or recesses to mate with the bridging element 30.

The micro-tube 20 of the embodiments shown in FIGS. 3-5 may terminate within the catheter reservoir 24 or may bypass the catheter reservoir 24 entirely. In one example the distal end of micro-tube 20 extends about 5-40 mm past distal connector 28. In another example the distal end of micro-tube 20 extends about 10-20 mm past distal connector 28. In another example the distal end of micro-tube 20 extends about 15 mm past distal connector 28.

Different catheters have different hub and reservoir sizes. The embodiments shown in FIGS. 3-7 can be thought of as a universal adapter since the micro-tube length does not have to be customized to fit various catheter hubs. Micro-tube 20 is placed as distally as possible within the catheter hub 22. Distal connector 28 and/or distal rotating element 34 is then pulled (spring bridging piece embodiment) or rotated (threaded bridging piece embodiment) so distal connector 28 (FIG. 3 embodiment) or distal rotating element 34 (FIGS. 4-6 embodiment) mates to the catheter hub. When pulled/rotated into this position, the rotating element 34 or distal connector 28 (depending on the embodiment) is then screwed over the catheter hub to secure the connection.

A method of using the universal delivery adapter of FIGS. 3-6 for delivery of a high viscosity liquid (e.g., a liquid embolic) is as follows: The catheter, microcatheter, or delivery device is flushed with saline and navigated to the target site. The catheter is flushed with solvent (e.g., a biocompatible solvent such as DMSO/dimethyl sulfoxide). The catheter hub 22 is filled with solvent (DMSO) in order to remove air bubbles and minimize chances of air bubble formation. The proximal connector 12 of the delivery adapter is connected to the syringe, and liquid embolic is injected through the delivery adapter to purge the delivery adapter of air. Once purged, the micro-tube 20 is placed within the catheter hub 22. Once the micro-tube 20 is placed within the catheter hub 22, the distal connector 28 (FIG. 3 embodiment) and/or distal rotating element 34 (FIGS. 4-6 embodiments) is pulled (spring bridging piece 30) or rotated (threaded bridging piece 30) to connect to the catheter. When pulled/rotated into this position, the rotating element 34 or distal connector 28 (depending on the embodiment) is then screwed over the catheter hub to secure the connection. Liquid embolic may then be delivered from the syringe, via the delivery adapter, to the target treatment site via the catheter once the catheter is navigated to the target treatment site.

Figure 7A:
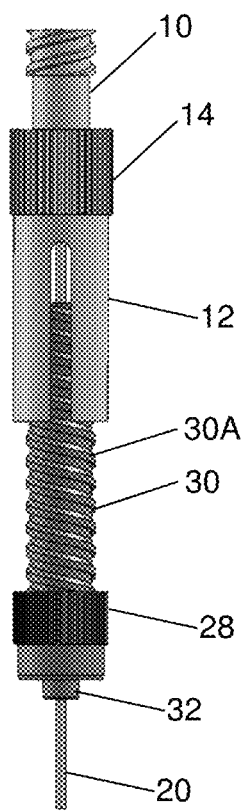
FIG. 7A depict a further embodiment of a delivery adapter according to the present invention.
Figure 7B:
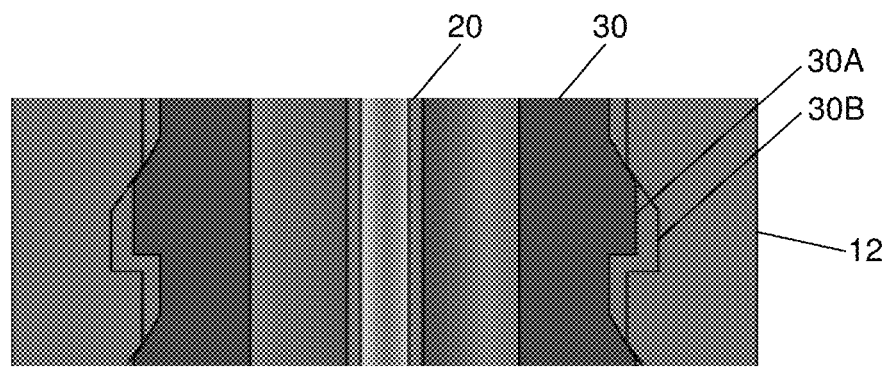
FIG. 7B illustrates a cross-sectional view of a thread configuration of the embodiment of FIG. 7A.

Referring to FIGS. 7A-7B, an additional embodiment of the adapter is shown. Proximal connector 12 mates with threaded bridging piece 30 via external threads 30A on the bridging piece and internal threads 30B on the proximal connector 12. However, the mating surfaces of the threads 30A, 30B are such that a threshold axial force (i.e., up or down) exerted on the proximal connector 12 will cause the walls of the proximal connector 12 to expand and to disengage the threads 30A/30B. This allows axial movement (either up or down) of the proximal connector 12 relative to the threaded bridging piece 30 in a ratchet-type action. Once the threshold axial force is removed, the walls of the proximal connector 12 will return to a normal position and the threads 30A, 30B will re-engage. In one preferred embodiment, the mating surfaces of the threads 30A/30B are ramped as illustrated in FIG. 7B.

In one embodiment, the proximal connector 12 is configured such that the user can squeeze together the outer top edges of the proximal connector 12 and thereby force the lower edges of the proximal connector to flex outwardly. This results in the disengagement of the threads 30A, 30B and allows the user to move the proximal connector 12 up and down freely. Once the desired position is reached, the user releases outer top edges of the proximal connector 12 and the lower edges of the proximal connector 12 return to the unflexed state and thereby threads 30A/30B reengage. The proximal connector 12 may adopt a slightly concave shape in this embodiment to enable such flexing in response to this squeezing pressure. In one example, a grasping portion (i.e. a roughened portion for the user to grip) can be included on the proximal connector 12 where the user would squeeze to initiate the flexing in order to freely move proximal connector 12.

Continuing to refer to FIGS. 7A, 7B, in use, the user determines the desired distance for the microtube 20 to extend beyond the distal connector 28. The user then exerts an axial force on the proximal connector 12 in the manner described above to move the proximal connector 12 and its attached microtube 20 to the aforesaid distance. The user can "fine tune" the desired distance through rotation of the proximal connector 12 relative to the threaded bridge piece 30. The adapter is then ready for inserting the microtube 20 into the catheter hub. The user then fastens the catheter to the adapter via screwing the distal connector 28 onto the catheter hub (e.g., via a luer lock connection). The user also attaches the syringe to the luer lock 10 at the top of the proximal connector 12.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An adapter comprising:
a first connector adapted for connection to a syringe;
a second connector independent of the first connector adapted for connection to a catheter hub; and
a tube extending from and distally beyond the first connector;
a position of the second connector adjustable over the tube.

2. The adapter of claim 1 wherein the tube extends through and beyond the second connector.

3. The adapter of claim 1 wherein the second connector is independently rotatable relative to the first connector.

4. The adapter of claim 1 wherein the tube extends through and beyond the second connector such that an end of the tube bypasses a reservoir of the catheter hub when the second connector is connected to the catheter hub.

5. The adapter of claim 1 wherein the tube extends through and beyond the second connector such that an end of the tube is positioned within a reservoir of the catheter hub when the second connector is connected to the catheter hub.

6. The adapter of claim 1 further comprising a bridging piece positioned between the first connector and the second connector.

7. The adapter of claim 6 wherein the bridging piece comprises threads.

8. The adapter of claim 6 wherein the bridging piece comprises a spring.

9. The adapter of claim 6 wherein the bridging piece comprises a deformable portion.

10. An adapter comprising:
a first connector adapted for connection to a syringe;
a second connector independent of the first connector adapted for connection to a catheter hub; and
a tube extending from the first connector through and distally beyond the second connector; and
a position of the second connector adjustable over the tube.

11. The adapter of claim 10 wherein the second connector is independently rotatable relative to the first connector.

12. The adapter of claim 10 wherein an end of the tube bypasses a reservoir of the catheter hub when the second connector is connected to the catheter hub.

13. The adapter of claim 10 wherein an end of the tube is positioned within a reservoir of the catheter hub when the second connector is connected to the catheter hub.

14. The adapter of claim 10 further comprising a bridging piece positioned between the first connector and the second connector.

15. The adapter of claim 14 wherein the bridging piece comprises threads.

16. The adapter of claim 14 wherein the bridging piece comprises a spring.

17. The adapter of claim 14 wherein the bridging piece comprises a deformable portion.

18. An embolic delivery system comprising:
a syringe containing an embolic material; and
an adapter comprising:
a first connector adapted for connection to the syringe;
a second connector independent of the first connector adapted for connection to a catheter hub; and
a tube extending from the first connector through and distally beyond the second connector.

19. The embolic delivery system of claim 18 wherein a position of the second connector is adjustable over the tube.

20. The embolic delivery system of claim 18 wherein the second connector is independently rotatable relative to the first connector.

21. The embolic delivery system of claim 18 wherein an end of the tube bypasses a reservoir of the catheter hub when the second connector is connected to the catheter hub.

22. The embolic delivery system of claim 18 wherein an end of the tube is positioned within a reservoir of the catheter hub when the second connector is connected to the catheter hub.

23. The embolic delivery system of claim 18 further comprising an adjustment portion positioned between said first connector and said second connector configured to allow adjustment of a distance between said first connector and said second connector.

24. The embolic delivery system of claim 23 wherein the adjustment portion comprises threads.

25. The embolic delivery system of claim 23 wherein the adjustment portion comprises a spring.

26. The embolic delivery system of claim 23 wherein the adjustment portion comprises a deformable portion.

* * * * *